US 6,573,415 B2

(12) United States Patent
Hommeltoft et al.

(10) Patent No.: US 6,573,415 B2
(45) Date of Patent: Jun. 3, 2003

(54) PROCESS FOR THE PREPARATION OF MONO ALKYL AROMATIC COMPOUNDS

(75) Inventors: Sven Ivar Hommeltoft, Hillerød (DK); Karsten Laurents, Kgs Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 8 days.

(21) Appl. No.: 09/933,412

(22) Filed: Aug. 20, 2001

(65) Prior Publication Data

US 2002/0045788 A1 Apr. 18, 2002

(30) Foreign Application Priority Data

Aug. 28, 2000 (DK) ........................... 2000 01272

(51) Int. Cl.$^7$ .............. C07C 2/70; C07C 2/68
(52) U.S. Cl. ............... 585/458; 585/462; 585/474
(58) Field of Search .................. 585/458, 462, 585/474

(56) References Cited

U.S. PATENT DOCUMENTS

| 4,288,646 A | 9/1981 | Olah |
| 4,547,474 A | 10/1985 | Olah |
| 4,547,604 A * | 10/1985 | Olah ........................... 585/458 |
| 4,613,723 A | 9/1986 | Olah |
| H1305 H * | 5/1994 | Townsend et al. ............ 44/449 |
| 5,959,169 A | 9/1999 | Hommeltoft |

FOREIGN PATENT DOCUMENTS

| AU | 491 575 | 10/1975 |
| EP | 0 537 389 | 4/1993 |
| EP | 0 538 518 | 4/1993 |
| EP | 0748784 A1 | 12/1996 |

* cited by examiner

*Primary Examiner*—Thuan D. Dang
(74) *Attorney, Agent, or Firm*—Dickstein Shapiro Morin & Oshinsky, LLP

(57) ABSTRACT

Process for the mono alkylation of a hydrocarbon substrate containing aromatic hydrocarbon compounds comprising contacting the aromatic substrate with an alkylating agent consisting of a mixture of olefinic compounds and poly-alkylated aromatic compounds in presence of a fluorinated sulphonic acid.

3 Claims, No Drawings

PROCESS FOR THE PREPARATION OF MONO ALKYL AROMATIC COMPOUNDS

BACKGROUND OF THE INVENTION

1. Field of the Invention

The present invention relates to a process for the preparation of mono alkyl aromatic compounds.

2. Brief Description of the Related Art

Benzene and other aromatic hydrocarbons are readily alkylated with olefins using a catalyst comprising a fluorinated sulphonic acid being supported on polar porous contact material. U.S. Pat. No. 5,959,169 discloses a process to remove aromatic hydrocarbons from a hydrocarbon mixture by selective alkylation of the noxious unsubstituted aromatic compounds with an olefinic alkylating agent in the presence of a catalyst consisting of a fluorinated alkyl sulphonic acid on a silica containing support material.

In a mixed stream of hydrocarbons containing aromatic compounds it is desirable to achieve high conversion with maximum selectivity to mono alkylated products. However, the alkylation reaction produces not only the desired mono alkylated product, but also products in which two or more alkyl groups are introduced. This problem is particularly important under conditions with high conversion of the aromatic feedstock.

SUMMARY OF THE INVENTION

It has been observed that fluorinated sulphonic acids including trifluoromethanesulphonic acid supported on a polar porous support material are capable of catalysing trans-alkylation reactions in which the poly-alkylated aromatic by-products are reacted with non-alkylated aromatic compounds to produce mono-alkylated aromatic compounds.

In accordance with the above finding, this invention is a process for the mono-alkylation of a aromatic hydrocarbon substrate in presence of a fluorinated sulphonic acid by contact of the aromatic substrate with an alkylating agent consisting of a mixture of olefinic compounds and poly-alkylated aromatic compounds.

The process according to the invention is in particular useful in the removal of benzene from reformat gasoline. With the tightening specifications on benzene content of gasoline it is desirable to convert benzene to less noxious alkyl derivatives such as ethyl or isopropyl benzene. These compounds have high octane numbers and alkylation of benzene to these compounds increases the octane value of the product. Poly-alkylated benzene being employed in the inventive process as alkylating agent such as tri-isopropyl benzene or triethyl benzene boil at temperatures being outside the range of compounds to be desirable to include those compounds into gasoline.

In the following examples the invention will be disclosed in more detail.

DETAILED DESCRIPTION OF THE PREFERRED EMBODIMENTS

EXAMPLES

Comparison Example 1

A stream of C6 distillate cut from reformat containing 30% benzene was alkylated with an alkylating agent consisting of solely propene. The alkylation reaction was carried out in a 100 ml reactor filled with silica gel on loaded with 10 g of trifluoromethanesulphonic acid catalyst. The reactor was submerged in a bath for temperature control.

The reaction was performed at 80° C. with total feed flow of 2.5 g/min. using various molar olefin/benzene ratios. The results are shown in Table 1.

The results indicate high conversion rate of benzene with a low selectivity to isopropyl benzene, when using propene as the sole alkylating agent in the reaction.

TABLE 1

Alkylation of benzene with propene at 80° C.

| | | | |
|---|---|---|---|
| Propene/benzene molar ratio | 1:1 | 2:1 | 3:1 |
| Benzene conversion, % | 52 | 72 | 92 |
| Composition of aromatics in product: | | | |
| Benzene, % wt | 33 | 15 | 3 |
| Isopropyl benzene, % wt | 25 | 15 | 4 |
| Di- and poly-isopropyl benzenes, % wt | 42 | 70 | 93 |

Example 2

Alkylation of benzene in presence of poly-alkylated benzene and propene alkylating agent according to a specific embodiment of the invention.

The same reactor as above was used but in this Example 20 g trifluoromethanesulphonic acid supported on silica gel was used as catalyst. A feed containing the same C6 cut of reformat as disclosed above but mixed with di- or tri-isopropyl benzene and propene was reacted at the below summarized conditions. The results are shown in Table 2.

TABLE 2

Alkylation of benzene with propene and di- and tri-isopropyl benzene

| | | | | |
|---|---|---|---|---|
| Temperature, ° C. | 80 | 110 | 80 | 110 |
| Propene/benzene molar ratio | 1:2 | 1:2 | 1:2 | 1:2 |
| Benzene conversion, % | 35 | 44 | 39 | 41 |
| Feed | | | | |
| Propene, % wt | 5.2 | 3.6 | 4.6 | 4.6 |
| Benzene, % wt | 23 | 23 | 22 | 22 |
| Isopropyl benzene, % wt | 0 | 0 | 0 | 0 |
| Di-isopropyl benzene, % wt | 0 | 0 | 21 | 21 |
| Tri-isopropyl benzene, % wt | 17 | 21 | 0 | 0 |
| Residual hydrocarbons | balance | balance | balance | balance |
| Product | | | | |
| Propene, % wt | 0 | 0 | 0 | 0 |
| Benzene, % wt | 15 | 13 | 14 | 13 |
| Isopropyl benzene, % wt | 7 | 9 | 8 | 11 |
| Di-isopropyl benzene, % wt | 6 | 11 | 19 | 18 |
| Tri-isopropyl benzene, % wt | 15 | 12 | 6 | 4 |
| Residual hydrocarbons | balance | balance | balance | balance |

As apparent from the above results, there is a significant conversion of the poly-alkylated benzene in the feed and an increased productivity of isopropyl benzene. Poly-alkylated aromatic compounds can be recycled to the reactor to react with benzene in a trans-alkylation reaction to form the desired mono alkylbenzene product.

What is claimed is:

1. A process for the mono-alkylation of a hydrocarbon substrate containing aromatic hydrocarbon compounds comprising contacting the hydrocarbon substrate with an alkylating agent consisting of a mixture of olefinic compounds and polyalkylated aromatic compounds in the presence of a fluorinated sulphonic acid to thereby produce a mono-alkylated aromatic compound.

2. The process according to claim 1, wherein the hydrocarbon substrate is reformat gasoline.

3. The process according to claim 1, wherein the polyalkylated aromatic compounds includes tri-isopropyl benzene and/or triethyl benzene.

* * * * *